United States Patent [19]
Johnson

[11] Patent Number: 4,680,312
[45] Date of Patent: Jul. 14, 1987

[54] STABLE PROSTAGLANDIN E GELS UTILIZING COLLOIDAL SILICON DIOXIDE AS A GEL-FORMING AGENT

[75] Inventor: Brian S. Johnson, Crawley, United Kingdom

[73] Assignee: The Upjohn Company, Kalamazoo, Mich.

[21] Appl. No.: 674,357

[22] Filed: Nov. 21, 1984

Related U.S. Application Data

[63] Continuation of Ser. No. 613,006, May 21, 1984, abandoned, which is a continuation of Ser. No. 470,656, Feb. 28, 1983, abandoned.

[30] Foreign Application Priority Data

Mar. 22, 1982 [GB] United Kingdom ............. 8208322

[51] Int. Cl.$^4$ .................... A61K 31/19; A61K 31/557
[52] U.S. Cl. ..................................... 514/573; 514/944
[58] Field of Search ................................ 514/573, 944

[56] References Cited

U.S. PATENT DOCUMENTS

| | | | |
|---|---|---|---|
| 3,749,800 | 7/1973 | Stehle et al. | 424/318 |
| 3,816,393 | 6/1974 | Hayashi et al. | 260/209 R |
| 3,826,823 | 7/1974 | O'Rourke et al. | 424/80 |
| 3,829,579 | 8/1974 | Stehle et al. | 424/312 |
| 3,927,197 | 12/1975 | Monkhouse | 424/45 |
| 3,966,962 | 6/1976 | Yalkowsky | 424/305 |
| 4,211,793 | 7/1980 | Lodhi et al. | 424/305 |
| 4,351,846 | 9/1982 | Matsumoto et al. | 424/317 |
| 4,390,548 | 6/1983 | Yamato et al. | 424/321 |

FOREIGN PATENT DOCUMENTS

| | | |
|---|---|---|
| 881351 | 5/1980 | Belgium . |
| 0016652 | 3/1980 | European Pat. Off. . |
| 0016654 | 3/1980 | European Pat. Off. . |
| 143516 | 11/1979 | Japan . |

OTHER PUBLICATIONS

Calder, A. A., et al., "Ripening of a Cervix with Extra Amniotic Prostaglandin E$_2$ in Viscous Gel Before Induction of Labor," Brit. J. OB/GYN, 84:264–268 (1977).

Eros, I., et al., "Applications of Colloidal Silicon Dioxide in Pharmaceutical Technology, II, Gysgyszereszet 19(8), 290–5 (1975), Chem. Abstracts 83:18331q (1975).

M. Sherriff and R. P. Enever, "Rheological and Drug Release Properties of Oil Gels Containing Coloidal Silicon Dioxide," J. Pharm. Sci., 68(7), 842–845 (1979).

Primary Examiner—Douglas W. Robinson
Attorney, Agent, or Firm—R. A. Armitage

[57] ABSTRACT

The present invention provides an improved class of stable gels of prostaglandin E compounds prepared from solutions of prostaglandin E compounds in a pharmaceutically acceptable, stabilizing organic solvent, e.g., triacetin, gelled by the addition of colloidal silicon dioxide.

1 Claim, No Drawings

STABLE PROSTAGLANDIN E GELS UTILIZING COLLOIDAL SILICON DIOXIDE AS A GEL-FORMING AGENT

DESCRIPTION

This application is a continuation of Ser. No. 06/613,006 filed 05/21/84, which is a continuation of Ser. No. 06/470,656 filed 02/28/83, both now abandoned.

BACKGROUND OF THE INVENTION

The present invention relates to novel compositions of matter and methods for using them as pharmaceutical agents. More particularly, the present invention relates to novel solutions of certain relatively unstable prostaglandins (prostaglandin E compounds), known to be useful for a wide variety of pharmacological purposes. Most particularly, the present invention relates to gelled solutions of these E-type prostaglandins wherein the gelling agent is colloidal silicon dioxide and the solvent within which said prostaglandin E compound is dissolved is an organic solvent, especially triacetin.

Prostaglandins are a family of cyclopentane-containing fatty acids. Typically these cyclopentane derivatives contain two side chains attached to adjacent positions of the cyclopentane ring (C-8 and C-12) in a trans configuration with respect to one another. In the natural prostaglandins the side chain at C-8 is carboxyl-terminated, contains seven carbon atoms and is attached in the α-configuration when this side chain is drawn in the conventional manner. The C-12 side chain is ω-alkyl terminated, substituted at C-15 by an α-hydroxyl group and attached in the β configuration. The carbon atoms of the cyclopentane ring adjacent to the attachment of these side chains are substituted with oxygenated functional groups in the PGE compounds. Specifically, in the naturally occurring PGE compounds the carboxyl-terminated side chain is attached to the cyclopentane ring at a position adjacent to an oxo group, while the position adjacent to the other side chain is substituted by an hydroxyl group. Hence, prostaglandin $E_2$ can be represented by the structure of formula I in which carbon atom numbering is given. For a more complete description of the PGE compounds, refer to the definition of "prostaglandin-like compounds of the PGE-type" set forth in U.S. Pat. No. 3,966,962, incorporated here by reference. Accordingly, the PGE compounds, i.e., the β-hydroxy ketones, includes such substances as $PGE_2$, $PGE_1$, 15-methyl-$PGE_2$, (15R)-15-methyl-$PGE_2$, 16,16-dimethyl-$PGE_2$, 17-phenyl-18,19,20-trinor-$PGE_2$, 16-phenoxy-17,18,19,20-tetranor-$PGE_2$, 15-cyclohexyl-16,17,18,19,20-pentanor-$PGE_2$, (11S),20-dimethyl-$PGE_2$, and the like.

The use of organic solvents, especially dry organic solvents, as a means of stabilizing PGE compounds is likewise known in the art. For example, U.S. Pat. No. 3,966,962, referred to above, discloses the use of glyceryl triacetate or triacetin as a stabilizing solvent for $PGE_2$ and similar PGE compounds.

Dipolar aprotic solvents such as N,N-dimethylacetamide (DMA), are also known stabilizers of PGE compounds. See U.S. Pat. No. 3,829,579. In addition to these organic solvents, other materials such as triethyl citrate have demonstrated an ability to stabilize PGE compounds. See U.S. Pat. No. 4,211,793.

Protic organic solvents are also known stabilizers of PGE compounds. In this regard, alcohols and glycols are known to be useful stabilizing solvents. See U.S. Pat. No. 3,749,800. See also U.S. Pat. No. 3,927,197, describing tertiary alcohol stabilization of PGE compounds.

In addition to the use of organic solvents for the stabilization of prostaglandins, further known in the art are hydrophylic gels, especially starchy gels which stabilize PGE compounds embedded there within. In this regard, cyclodextrin clathrates, especially β-cyclodextrin clathrates are known as stabilizers for PGE compounds. See U.S. Pat. No. 3,816,393.

See also Calder, A. A. et al., "Ripening of a Cervix with Extra Amniotic Prostaglandin $E_2$ in Viscous Gel Before Induction of Labor", British Journal of Obstetrics and Gynecology 84:264–268 (1977) which describes the use of hydroxyethyl methyl cellulose as a gelling agent for $PGE_2$. Moreover the use of gelled cellulose as a stabilizing agent for $PGE_2$ is described in Derwent Farmdoc CPI No. 91634B/51, abstracting Japanese Kokai No. 143,516, published Nov. 8, 1979.

Besides starchy materials, polymeric materials have also been reported to be effective solid or gelled stabilizing agents for for example, the use of polyvinyl pyrolidone (PVP) to stabilize prostaglandin E compounds is reported in U.S. Pat. No. 3,826,823. See also the use of polyethylene oxide cross linked with urethane group for prostaglandin formulation described in European published application Nos. 16,652 and 16,654. Finally see also the carbohydrate polymer or cross linked carbohydrate polymers described in Derwent Farmdoc CIP No. 43291C/25 abstracting Belgian Pat. No. 881,351.

The use of colloidal silica dioxide as a gelling agent for organic solvents is also known. See Eros, I., et al, "Applications of Colloidal Silicon Dioxide in Pharmaceutical Technology, II, Gel-forming Properties of Aerosil", Gysgyszereszet 19(8), 290–5 (1975); Chem. Abstracts 83:183331q (1975). In particular the use of colloidal silica dioxide with organic solvents for preparing gels containing pharmaceutically active materials is also known. See M. Sherriff and R. P. Enever, "Rheological and Drug Release Properties of Oil Gels Containing Coloidal Silicon Dioxide," J. Pharm. Sci., 68(7), 842–5 (1979).

PRIOR ART

A stable dosage form of a PGE compound in a pharmaceutically acceptablizing organic liquid is known. See U.S. Pat. No. 3,966,962 describing the stabilization of various PGE compounds in a solution of triacetin. Utilization of gels, especially hydrophylic gels, in the stabilization of PGE compounds is likewise known. See the reference cited above. Finally the use of colloidal silica dioxide as a gel forming additive to pharmaceutically acceptable stabilizing organic liquids is known. Moreover the application of such gels to the delivery of pharmaceuticals is known.

SUMMARY OF THE INVENTION

The present invention particularly comprises:

In a stable dosage form of PGE compound consisting essentially of a solution of said PGE compound in a pharmaceutically acceptable stabilizing organic liquid, an improvement which comprises:

colloidal silicon dioxide (CSD) as a gel-forming additive thereto in a concentration sufficient to induce a free flowing gel.

The present invention further comprises an improvement wherein the pharmaceutically acceptable stabilizing organic solvent is a glycerol ester. More particularly, the present invention provides the improvement wherein the glyceryl ester is triacetin.

Further, with respect to such a triacetin-based formulation the present invention further provides the improvement wherein the colloidal silicon dioxide percentage by weight in the stable dosage form is from about not less than 3 to about not more than 15 percent by weight. The preferred percentage by weight is about 8. Lesser percentages by weight result in gels of lesser viscosity which may not be sufficiently elegant in actual clinical application. Gels whose percentage of CSD by weight is greater than 8 are also useful but result in more viscous gels of reduced extrudability. Since such gels tend to increase in viscosity upon storage, percentages greater than 8 are especially useful when gels are to be used promptly following formulation.

The stable dosage forms provided in accordance with the present invention are used for the same purposes and by the same method as the prior art PGE compounds in a pharmaceutically acceptable stabilizing organic solvent with the difference that the present forms are rendered more adaptable for formulation and use by virtue of being in the gel form. Accordingly, dosage forms in accordance with the present invention are used for various purposes described in U.S. Pat. No. 3,966,962, incorporated here by reference. However, the present gel composition are particularly advantageous in that these materials are more readily handled and formulated than liquids. Moreover, for example, when used for intravaginal, transcervical or intracervical, or extraamniotic injection, the gel is prepared under sterile conditions and administered via syringe. Advantageously, the present invention provides gels whose physical characteristics and ambient temperature permit free and unobstructed flow when so administered.

More particularly, the present invention provides a highly advantageous method of effecting cervical ripening utilizing extraamniotic administration of $PGE_2$ in a viscous gel. The methodology of employing $PGE_2$ in such viscous gels for extraamniotic cervical ripening is described in Calder, A. A., et al., British Journal of Obstetrics and Gynecology 84:264–268 (1977), cited above.

Unlike prior art gels which required reconstitution prior to use, the present invention provides stabilized gels which can be manufactured under sterile conditions, packaged and distributed to hospitals or other users without the need for reconstitution, i.e., the addition of water, prior to use. Particularly, prostaglandin $E_2$ prepared in the novel dosage form of the present invention can exhibit a prolonged shelf-life, i.e., greater than one year, during storage at ambient temperature. Further, unlike hydrophilic gels of the prior art the present gels can maintain the physical integrity of the gel more completely upon administration and therefore, unlike these prior art gels, be withdrawn if necessary from the patient following extraamniotic, transcervical application.

In preparing the gels of the present invention, the PGE compound is first dissolved in the selected organic solvent by conventional means. For example, the dissolution of $PGE_2$ and triacetin can be readily achieved using a mixer fitted with a small disintegrating head. During the mixing process, which usually runs to completion over the course of several minutes, cooling may be required in order to prevent heat generated by the mixing process from decomposing the $PGE_2$.

Thereafter the colloidal silicon dioxide is incorporated into the resulting solution by combining these two ingredients in a single vessel and mixing with a stirrer. Gelling under these conditions is ordinarily effected over the course of several minutes.

The preparation of sterile product can be accomplished by an ultrafiltration of the PGE compound in the organic solvent into a sterile area. Subsequently the colloidal silica dioxide can be heat sterilized and incorporated into the sterilized PGE compound solution.

In accordance with the present invention, pharmaceutical grades of both the organic solvent and colloidal silicon dioxide must be selected. For example, when triacetin is the selected organic solvent, USP or food grade quality material, particularly material known to be low in heavy metal compound content, is readily employed. Moreover, employing triacetin low in metal ion content results in improved stability of the resulting PGE gel.

Similarly, colloidal silica dioxide is available as a pharmaceutical grade material. For example, Cabot Corporation markets CAB-O-SIL M5 colloidal silica dioxide, a material used in oral pharmaceutical formulations of prostaglandin $E_2$ (PROSTIN E2 compressed tablets, Upjohn). Similarly AEROSIL 200 and AEROSIL FK 320 are similar grades of colloidal silicon dioxide marketed by Degussa.

Since some organic solvents are incompatible with the use of plastic packaging material, e.g., polypropylene syringes, ordinarily a glass syringe is employed and a preselected amount of the gel placed there within. However, when triacetin is employed as the organic solvent, the preferred syringe is a plastic syringe, e.g., polypropylene or high density polyethylene. The use of such plastic syringes is preferred in order to avoid the leaching of impurities into the formulation from the rubber-containing parts of glass syringes.

Alternatively, conventional gelatin capsules may be utilized in formulating these gels into their finished pharmaceutical form. For example hard gelatin capsules are especially useful.

The pharmaceutically acceptable stabilizing organic liquid or solvents utilized in accordance with the present invention are those which are relatively non-toxic and non-irritant to body tissues which they contact and those having a capacity to stabilize PGE compounds when placed in solution therewith. One especially useful group of materials for this purpose are glyceryl esters. Such compounds are either mono-, bis-, or tris-esters of glycerol and are known in the art and prepared by methods readily known in the art. For example, triacetin is one such substance. Dipolar aprotic solvents, such as DMA referred to above, are also useful liquids for this purpose. Similarly, other polyol esters such as triethyl citriate are known to be useful in pharmaceutically acceptable stabilizing organic liquids for use in accordance in the present invention.

Alcohols represent another, although less preferred pharmaceutically acceptable stabilizing organic liquid inasmuch as the lower polyols, such as ethanol, are subject to evaporative loss of volume thereby complicating unnecessarily formulation of the resulting gel. Accordingly, useful pharmaceutically acceptable stabilizing organic liquids or solvents utilized in accordance with the present invention include numerous known organic solvents for the stabilization of prostaglandin all of the following chemical compounds.

The stabilizing liquid to be employed in the present invention must also be pharmaceutically acceptable in the sense that the quantities employed must be essentially non-toxic and well tolerated by the animal or patient being treated. The examples above described such liquids. Organic solvents such as benzene are, for example, unsuitable for reasons of toxicity.

The amount of colloidal silica dioxide employed in any gel depends on the nature of the organic liquid employed. However, in general, the minimum amount of colloidal silicon dioxide necessary is that required to give necessary minimum viscosity to the selected liquid. Ordinarily, gels are preferred which are sufficiently viscous to remain in place when administered. Similarly, the maximum precentage by weight of colloidal silicon dioxide desired is that which defines the maximum desired viscosity of the gel and ordinarily limited by the ability of the gel to be extruded through syringes, catheters and the like. Accordingly a fairly narrow range of values for the precent by weight of silicon dioxide of the weight of the final gel is employed. For example, when triacetin is the pharmaceutically acceptable stabilizing organic solvent, the preferred range for the colloidal silicon dioxide is 3–15% by weight of the resulting gel.

DESCRIPTION OF THE PREFERRED EMBODIMENTS

The operation of the present invention is more completely understood by the following example.

EXAMPLE 1

Colloidal silicon dioxide gel solution of $PGE_2$ in triacetin

Gels are prepared with between 0.25 mg and 3.0 mg of $PGE_2$ per 3 g or 2.5 ml of gel. The following ingredients are used:

(a) $PGE_2$ (dinoprostone PROSTIN E2, Upjohn) 0.25 mg–3.0 mg.
(b) colloidal silicon dioxide NF 200 mg–300 mg.
(c) triacetin USP 2.7 g–2.8 g.

$PGE_2$ is dissolved in triacetin using a Silverson mixer fitted with a ½ inch disintegrating head. After mixing for 15 min using an ice bath to prevent heat disintegration of $PGE_2$, colloidal silicon dioxide is then incorporated into the $PGE_2$ solution until the desired viscosity is obtained by mixing the $PGE_2$/triacetin solution with the appropriate amount of silicon dioxide until the mixture is gelled. i.e., about 2 min. The gel thusly obtained is then packed in a 5 ml Hypac SCF glass syringe (Becton Dickinson) which has been washed, silicized, and sterilized. Preferred, however, is the 5 ml PharmaPlast polypropylene syringe which has been sterilized by exposure to ethylene oxide.

Alternatively the gel is fitted into an appropriately sized empty gelatin capsules.

FORMULA I

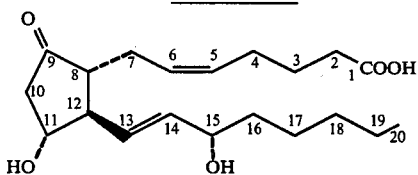

I claim:

1. In a stable dosage form of $PGE_2$ consisting essentially of $PGE_2$ in triacetin, an improvement which comprises:
colloidal silicon dioxide (CSD) as a gel forming additive thereto in a concentration by weight of CSD in said stable dosage form from about not less than 8 percent to about not more than 15 percent.

* * * * *